United States Patent [19]

Ecke, Jr.

[11] Plant 4,808

[45] Jan. 19, 1982

[54] POINSETTIA NAMED V-14 PINK

[75] Inventor: Paul Ecke, Jr., Encinitas, Calif.

[73] Assignee: Paul Ecke Ranch, Encinitas, Calif.

[21] Appl. No.: 185,121

[22] Filed: Sep. 5, 1980

[51] Int. Cl.[3] ..... A01H 5/00
[52] U.S. Cl. ..... Plt./86
[58] Field of Search ..... Plt./86

*Primary Examiner*—Robert E. Bagwill

*Attorney, Agent, or Firm*—Rummler and Snow

[57] ABSTRACT

A new variety of poinsettia plant having the important characteristics of the red variety Gutbier's V-14 (U.S. Plant Pat. No. 4,384), known commercially as "Glory", including the unique ability to produce numerous side shoots on its stem and the production of bracts with short petioles which prevent tubing, but distinguished by the fact that its bracts have a distinctive pink color.

1 Drawing Figure

BACKGROUND OF THE NEW PLANT

This new plant originated as a mutation of Gutbier's V-14 "Glory" (U.S. Plant Pat. No. 4,384) which occurred in my greenhouses at Encinitas, Calif., in the course of my breeding efforts and trials carried on with the object of obtaining new and better poinsettia varieties for the commercial market. This particular plant was selected by me for trial because of its interesting pink color and it was propagated by me through several successive generations, by means of cuttings, at Encinitas, Calif., which demonstrated that its novel and distinctive characteristics hold true from generation to generation and appear to be firmly fixed.

DESCRIPTION OF THE DRAWINGS

My new pink poinsettia cultivar is illustrated by the accompanying full color photographic drawings, the upper one of which shows a full face view of a mature bloom of this variety and the lower one of which is a view showing the potted plant in full bloom, the colors shown being as nearly true as can be reasonably expected from conventional photographic procedures.

DESCRIPTION OF THE NEW PLANT

The following is a detailed description of this new poinsettia plant, as observed in greenhouse in Encinitas, Calif., with the color designations according to the R.H.S. Colour Chart published by The Royal Horticultural Society of London, England.

THE PLANT

Origin: Mutation.

Parentage: Gutbier's V-14 (U.S. Plant Pat. No. 4,384).

Classification:

*Botanic.*—*Euphorbia pulcherrima.*

*Commercial.*—Greenhouse poinsettia.

Form: Shrub.

Height: Medium.

Growth habit:

*As a single stem.*—Upright and vigorous with self-branching side shoots.

*As a branched plant.*—Upright with very many stems producing a bushy, full appearance.

Growth rate: Very fast. Rooting occurs in about 10 to 15 days under automatic mist with the plant blooming in about 9 to 10 weeks at a night temperature of 17° to 19° C. during October and November.

Foliage: Alternate and horizontal, with medium persistence and in normal abundance.

*Leaf size.*—Medium. About 4 to 6 inches long and about 2½ to 4½ inches wide.

*Leaf shape.*—Substantially ovate, some with acuminate tip. Most leaves have one or two serrations on each side.

*Aspect.*—Upper side — dull with indented veins. Under side — dull with ordinary veining.

*Color.*—Upper side — between RHS 137A and 147A. Under side — near 137C.

*Petioles.*—Green, often with pink tinge.

*Retention.*—The foliage lasts well when kept at a low room temperature, i.e. below 20° C., and with good light intensity.

Bracts: Generally about 15 to 20 in number, in overlapping arrangement and with a tight center providing a full effect.

*Size.*—Various, up to 7 inches long and 6 inches wide, some being as wide as they are long.

*Shape.*—Ovate-acuminate with substantially entire margins but with some indentations. Small bracts are elliptic in shape.

*Petioles.*—Quite short, from ¼ inch to about 1 inch long.

*Color.*—Upper side — between RHS 51B and 51C and with veins near 47D. Under side — near RHS 51C.

*Ribs and veins.*—Veins are of a light creamy color and protrude from the under side of the bracts.

*Retention.*—Medium persistence similar to that of the Eckespoint C-1 varieties.

This new variety of poinsettia plant retains substantially all of the important characteristics of its parent, Gutbier's V-14 "Glory" (U.S. Plant Pat. No. 4,384). The plant is particularly distinguished by the unique pink coloration of its bracts and the fact that the bracts are numerous, tightly centered and in overlapping arrangement which, in the case of multi-stemmed plants, provides a full and compact display of pink color, which affords a very unique and lovely display.

I claim:

1. A new and distinctive poinsettia plant, substantially as herein shown and described, distinguished by the unique pink color of its numerous bracts, which are tightly centered and in overlapping relation to provide a full, compact appearance in full bloom.

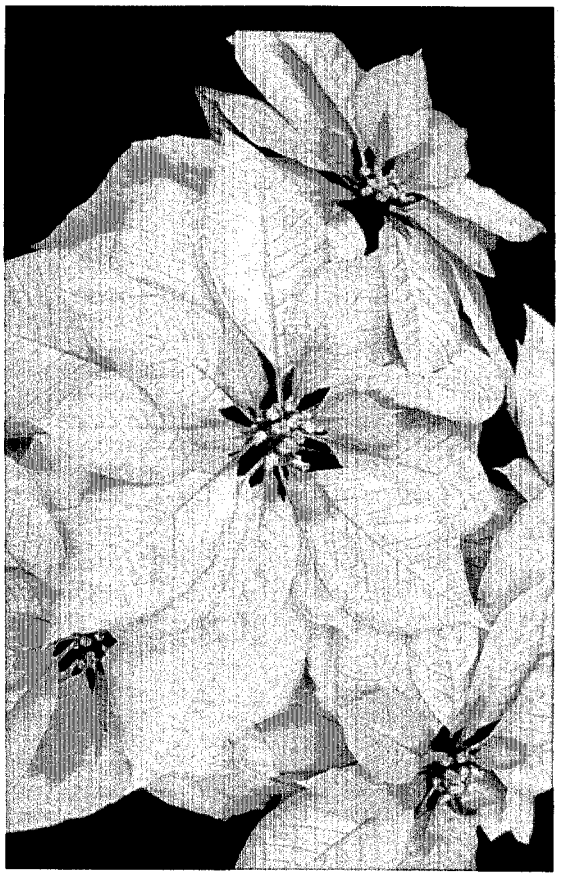
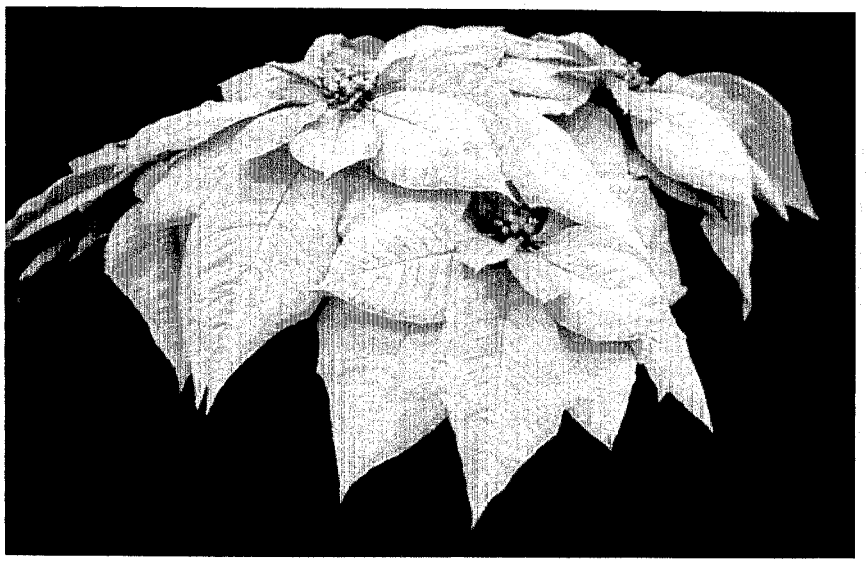

* * * * *